United States Patent [19]

Powell

[11] 4,089,834

[45] May 16, 1978

[54] WATER-RESISTANT MICRO-CAPSULAR OPACIFIER SYSTEM AND PRODUCTS

[75] Inventor: Mabrin P. Powell, Chicago, Ill.

[73] Assignee: Champion International Corporation, Stamford, Conn.

[21] Appl. No.: 322,629

[22] Filed: Jan. 11, 1973

Related U.S. Application Data

[62] Division of Ser. No. 55,925, Jul. 17, 1970, Pat. No. 3,779,941.

[51] Int. Cl.$^2$ .............................................. C08L 61/20
[52] U.S. Cl. ............................. 260/29.4 UA; 106/312; 252/316; 260/15; 260/28.5 A; 260/29.3; 260/855; 260/856; 264/4
[58] Field of Search ......... 260/29.3, 29.4 R, 29.4 UA, 260/15, 28.5 A, 855, 856; 264/4; 252/316; 106/312

[56] References Cited

U.S. PATENT DOCUMENTS

| 2,969,331 | 1/1961 | Brynko et al. | 424/16 |
| 3,418,656 | 12/1968 | Vassiliades | 424/19 |
| 3,459,128 | 8/1969 | Erdmann et al. | 260/29.3 |
| 3,615,791 | 10/1971 | Thomas et al. | 260/29.3 |
| 3,720,534 | 3/1973 | Macaulay et al. | 117/36.2 |
| 3,766,105 | 10/1973 | Chan | 260/29.4 UA |
| 3,779,941 | 12/1973 | Powell | 252/316 |

Primary Examiner—Lorenzo B. Hayes
Attorney, Agent, or Firm—Roylance, Abrams, Berdo & Kaul

[57] ABSTRACT

Microcapsules having controlled structural integrity are produced by a process which involves admixing a thermosetting condensation polymer-containing oily solution and a polymer-containing aqueous solution and causing a chemical reaction between the polymers at the resulting oil/water interface. The so-formed microcapsules have excellent water resistance and may be employed in the formation of opacifying agents in coatings and particularly in paint films.

11 Claims, No Drawings

WATER-RESISTANT MICRO-CAPSULAR OPACIFIER SYSTEM AND PRODUCTS

This is a division, of application Ser. No. 55,925 filed July 17, 1970, now U.S. Pat. No. 3,779,941.

This invention relates to the art of microencapsulation. More particularly, this invention relates to the production of water-resistant microcapsules and to microcapsular systems.

Microcapsular products have been employed extensively in a wide range of products, including pharmaceuticals, foods, cosmetics, adhesives, adhesives tapes, fertilizers, and the like. Additionally, microcapsules have been employed in the art of transfer-copy systems wherein minute droplets of a colorless dye intermediate material are dispersed or dissolved in an oil, encapsulated, and thereafter coated onto a transfer sheet. The transfer sheet is employed in combination with an underlying copy sheet having an absorbent coating thereon containing material which can react with the dye intermediate and form a visible colored mark. The pressure from an ordinary stylus or typewriter causes the capsules immediately adjacent thereto to rupture and release the dye intermediate which reacts with the underlying copy sheet at points where the microcapsules have been ruptured.

U.S. Pat. Nos. 3,418,250 and 3,418,656 to A. E. Vassiliades describe the production of microcapsules having walls formed of a thermosetting and/or a thermoplastic resinuous material. Such microcapsules are highly suitable for use in pressure-responsive, transfer-copy systems, and the like. The process for forming microcapsules involved in such patents involves admixing a water-immiscible oily material and/or water-and-oil-immiscible organic liquid solution of a thermoplastic resin with an aqueous medium thereby causing the resin to separate from solution in solid particle form about an nucleus of oily material.

Prior microencapsulation processes have involved, for example, the formation of an oil-in-water emulsion followed by the addition of an aqueous solution of a wall-forming polymeric material. In addition, such processes have utilized a cross-linking or curing agent that must be added in order to harden the capsular walls of the microcapsules. Still other encapsulation processes require the addition of acids in order to produce condensation and/or cause precipitation of the polymeric wall-forming material.

Likewise, microcapsules have been produced by a procedure involving interfacial polycondensation whereby two reactants are brought together at a reaction interface wherein polycondensation occurs to form a capsule shell consisting of a high molecular weight condensation polymer. This technique is described, for example, in U.S. Pat. No. 3,429,827 to Ruus. Another microencapsulation technique involving the addition polymerization of monomers is described in U.S. Pat. No. 2,969,330 to Brynko. Still another process for encapsulation described in U.S. Pat. No. 3,432,327 to Kan et al which describes the preparation of a pressure sensitive copying sheet coated with microcapsules formed by the interfacial reaction of polymeric substances at the interface of hydrophobic and hydrophilic liquids.

It has been proposed to employ air-containing microcapsules having an average particle size below about one micron as opacifying agents in coatings, on fibrous substrates, and in non-fibrous substrates. These microcapsular opacifying agents process an opacifying power substantially greater than any known inorganic pigment. The incorporation of microcapsular opacifiers into surface finishes, such as paints, requires that the opacifiers have additional properties including scrubability, freeze-thaw stability, and the like. Thus, the microcapsular opacifiers employed in surface coatings should desirably possess a high resistance to water in order that the painted surface withstand repeated washings, for example.

It has now been found that microcapsular opacifiers may be produced having excellent water-resistance, controlled wall strength, uniformity of particle size and which yield surface finishes having excellent hiding power when employed in surface coatings, such as paint films and the like. According to the present invention, a process is provided for the formulation of microcapsular precursor opacifiers which comprises admixing:

(a) a solution comprising an oil-soluble, partially condensed thermosetting condensation product in a water-immiscible oily material; and (b) an aqueous solution of a water-soluble polymeric material;

thereby forming an emulsion, said thermosetting condensation product and said water-soluble polymeric material being capable of interaction to form a solid, cross-linked resinous material, and subjecting said emulsion to conditions whereby said polymeric materials react to form microcapsules having solid capsular walls about a nucleus of said oily material. The precursor capsules are then treated to expel the oily core material and replace it with air.

Surprisingly, it has been discovered that by providing an oil-soluble, thermosetting condensation product wall-forming material in an oil phase and admixing this oily solution with a water-soluble polymer in an aqueous phase, microcapsular opacifiers are produced having unexpectedly good water resistance. By providing the thermosetting condensation product in the oil phase, its distribution is confined within the capsule and thus forms the inside of the capsule wall. In this manner, substantially all of this polymeric material is efficiently utilized. Prior processes have employed such resins in a water-soluble form. However, when employed in the aqueous phase, some of the polymer remains in the continuous phase of the emulsion after the capsules are formed. Thus, in the prior systems, where for example, the thermosetting resin is a formaldehyde condensation product, e. g., urea-formaldehyde, the water-soluble urea-formaldehyde has been employed in an aqueous solution and admixed with an aqueous solution of another polymeric material, e.g., methyl cellulose to form capsule walls, there is generally some urea-formaldehyde left on the outside of the capsules which remains in the aqueous phase. This unused, residual amount of urea-formaldehyde is inefficiently utilized as excess binder, rather than contributing to the capsule wall. In many cases this is undersirable, since it may reduce optical response when present as a binder. On the other hand, the urea-formaldehyde condensate of the present system is substantially entirely utilized in the formation of the capsule walls.

The oil-soluble, partially condensed, thermosetting condensation products of the present invention includes A-stage or B-stage resins, i.e., resins not having reached the infusible or insoluble stage. However, the B-stage resins are especially preferred for the purposes of the present invention.

Exemplary of suitable oil-soluble resins are the condensation reaction products of formaldehyde with phenols, such as, hydroxybenzene (phenol), m-cresol and 3,5-xylenol; carbamides, such as urea; triazines, such as melamine; amino and amido compounds, such as, aniline, p-toluenesulfonamide, ethyleneurea and guanidine; ketones, such as acetone and cyclohexanone; aromatic hydrocarbons, such as naphthalene; and heterocyclic compounds, such as, thiophene. Under the influence of heat, these resins change irreversibly from a fusible and/or soluble material into an infusible and insoluble material.

The preferred formaldehyde condensation products employed in this invention are partially-condensed melamineformaldehyde, phenol-formaldehyde and urea-formaldehyde resins. The B-stage melamine and urea-formaldehyde resins are especially preferred.

Oil-soluble partially condensed resins can be prepared easily according to conventional practices. For example, the compatibility of the partially condensed resin with various oily solvents can be influenced by alkylating the resin with an alkanol, such as butanol or a combination of butanol with a higher alkanol, such as octyl alcohol or the like. The preparation of a suitable oil-soluble melamine-formaldehyde and its modification with butanol is described on pages 460–461 of Preparative Methods of Polymer Chemistry, by Wayne R. Sorenson (Inter-Science Publishers, 1961), the disclosure of which is hereby incorporated by reference.

The substitution of a portion of the butanol alkylating agent by the higher alkanol increases the compatibility of the resin, e.g., melamine formaldehyde, with the hydrocarbon solvent. The properties of such melamine resins are described on pages 192 and 193 of Amino Resins, by John F. Blais (Reinhold Publishing Corp., N.Y., 1959).

Any suitable oily material may be employed in the preparation of the oily solution of the partially condensed formaldehyde condensation polymer of the present invention. As previously mentioned, the oily material in the precursor microcapsules is driven from the microcapsules and is replaced by air. The oily material of the present invention includes lipophilic materials which are preferably liquid, such as oils, which will not mix with water and which can be driven through the porous, solid walls of the present precursor microcapsules. The oily material may be a low melting fat or wax. However, oils are the preferred oily material, since they do not require special temperature maintenance during the production of the microcapsules. Furthermore, oils are more easily volatilized and driven through the micropores of the walls of the microcapsules.

In general, the lipophilic nucleus materials may be natural or snythetic oils, fats, and waxes or any combination thereof which can be removed from the microcapsules at the desired temperatures. Among the materials that can be employed in the process of the present invention are: aliphatic hydrocarbons, for example, heptane, octane, decane or mixtures of such materials, for example, mineral spirits products and the like.

The preferred oily materials for employment in the present invention are those oils having a fairly high vapor pressure (high volatility), so that they can be completely and easily expelled through the micropores of the solid-walled microcapsules over a wide range of temperatures, e.g., by the application of moderate amounts of heat, e.g., −32° to 180° C., preferably between about 0° to about 100° C. It is especially preferred to employ oils which can be driven from the microcapsules at temperatures conventionally employed in the drying of paper webs or paper coatings, e.g., about 85° C. Preferred oils for use in the present invention include mineral spirits, benzene, xylene, toluene, styrene monomer, turpentine, and oils having a like volatility.

The water-soluble polymeric material of the present invention which reacts chemically with the partially condensed formaldehyde condensation product dissolved in the oil phase, may be any suitable water-soluble polymer capable of reacting with the formaldehyde condensation polymer at the oil-water interface to form a solid microcapsular shell. Suitable water-soluble polymers which may be employed in the present invention include thermoplastic resins, such as polyvinyl alcohol, methyl cellulose, a styrene-maleic acid salt, e.g., the sodium or ammonium salt thereof, and the like. The preferred water-soluble polymer is a styrene-maleic acid ammonium salt.

The water-soluble polymeric material of the present invention functions as an emulsifying agent in addition to its being a wall-former. Accordingly, an added advantage of the present process is the absence of any requirement for an added emulsifier.

An oil-in-water emulsion is formed by admixing the oily solution of the formaldehyde condensation product and the aqueous polymeric solution under conditions of brisk agitation. Brisk agitation is employed in order to obtain very small droplets of the emulsion, and, ultimately, very small capsules. Thus, microcapsules having diameters ranging from about 0.1 to several hundred microns can be produced depending upon the degree of agitation. In order to produce suitable opacifying agents, the microcapsules produced by the process of the present invention must have an average particle size of below about one micron, and preferably between about 0.25 and about 0.8 micron. Agitation may be achieved by means of a high speed mixer or impeller, by ultrasonic waves or by other conventional means.

If desired, a relatively small amount, e.g., between about 0.5 and about 5 percent, preferably between about 2 and about 3 percent by weight of a natural or synthetic wax may be added to the oily solution of the thermosetting condensation product to further increase the water resistance of the capsular walls. Thus, a wax modifying agent, such as candilillia wax, caranauba wax, low molecular weight synthetic waxes, such as polyethylene and paraffin waxes may be added to the oily polymeric solution which, in combination with formaldehyde condensate remaining inside the microcapsule after the core solvent has been expelled through the permeable walls of the microcapsules, further increases the water resistance of the microcapsular walls.

After the formation of the oil-containing microcapsules, these opacifier precursors are treated to remove the oily core material and replace the same with air. Thus, for example, the precursor microcapsules may be heated to temperatures which cause the oily core material to volatilize and pass through the micropores in the solid walls of the capsules. In the case of microcapsular opacifiers to be used on fibrous substrates, the oily material may be driven from the microcapsules either before or subsequent to their being coated onto the substrate. For example, a dispersion of the oil-containing microcapsules may be spray-dried so as to provide air-containing microcapsules, which may be then coated onto the substrate.

The microcapsular opacifiers of the present invention are particularly useful in surface coatings where resistance to water is required. Thus, the instant opacifiers find particular application in paint formulations. The microcapsular opacifiers may be mixed with inorganic pigments and additional binders, such as a latex binder to form an aqueous paint system. Likewise, the opacifiers may be suspended in a solvent to produce a solvent-based paint system. These paint formulations possess a substantially greater hiding power than paint films of the same thickness which contain inorganic pigments, such as titanium dioxide as the opacifying agent. In addition, paint formulations containing the microcapsular opacifiers of the present invention possess scrubability, freeze-thaw stability and other properties equal to paint formulations containing commonly used titanium dioxide pigments.

Alternatives modes of providing paint systems containing the air-containing microcapsular opacifiers of the present invention may be utilized.

According to one mode of the present invention, an oily solution of a partially condensed formaldehyde condensation product, e.g., malamine-formaldehyde is admixed with an aqueous solution of a polymeric material, e.g., methyl cellulose, and emulsification is continued under conditions of brisk agitation until the desired particle size is obtained, e.g., below one micron. Emulsification is conducted, for example, at a temperature in the range of between about 25° and about 100° C., preferably between about 30° and about 40° C.

Next, the emulsion is heated to a temperature sufficient to induce a chemical reaction between the oil-soluble polymer and the water-soluble polymer at the emulsion interface. Suitable temperatures to cause such chemical interaction are, for example, between about 50° C. and about 100° C., preferably 50° C., depending upon the particular system involved.

According to this mode of the invention, the microcapsules are activated, i.e., the oily core material is driven off at this point in the system. This may be accomplished by spray-drying the precursor capsules, subjecting the capsules to a vacuum, or otherwise treating the capsules to drive the oily material from the interior of the microcapsules and replace it with air. It is especially preferred to spray-dry the capsules, thereby driving the oily material from the capsular core while promoting cross-linking of the capsule walls. Once the oily core has been replaced with air, the capsules may be fully cured. Suitable activation temperatures include between about ambient temperature and 210° C., for example.

The resultant opacifiers may be either dispersed in an aqueous paint system, or may be dispersed in a solvent and formed into a solvent based paint. Likewise, the precursor microcapsules may be dispersed with clay and binders to form an aqueous paint system and may be cured in the form of a film by heating, e.g., 200° C. for 10 minutes, or by curing the paint system, e.g., 30 days at ambient temperature.

According to a second mode of the invention the oil-containing microcapsular precursors are not activated immediately after their formation. Rather the precursor microcapsules are mixed with binders, such as clay and latex, to form an aqueous paint system. Next, the paint formulation is applied to the desired substrate to form aqueous paint film, and the paint film is dried at ambient or elevated temperatures to activate the precursor microcapsules and permit the oily core material to escape. In this manner, the opacifiers are produced in situ without the need for an additional activation step.

The following examples further illustrate the practice of the present invention. The percentages are by weight unless otherwise specified.

EXAMPLE 1

Twenty grams of a 50 percent by weight of a melamine formaldehyde solution in mineral spirits are diluted with 80 grams of mineral spirits to a total weight of 100 grams of solution. The melamine formaldehyde solution is emulsified with 150 grams of a 5 percent by weight aqueous solution of a copolymer of styrene-maleic acid (ammonium salt). Emulsification is continued until particles of the desired size and uniformity, viz., below about one micron, are obtained.

Next, the emulsion is heated to a temperature of 50° C. while under agitation for approximately 6 hours to induce an interfacial chemical reaction between the partially condensed formaldehyde condensation polymer and the styrene-maleic acid copolymer at the water/oil interface thereby forming microcapsules. A partial curing of the capsules is effected during the heating period. The extent of curing may be varied depending upon desired properties of the final product and its application.

EXAMPLE 2

The microcapsular dispersion produced in Example 1 is activated to remove the oily core by injecting the dispersion by means of a fine air feed nozzle into a spray drying chamber heated to a temperature of about 100° C. Optionally, the activated microcapsules may be subjected to a subsequent drying treatment in a fluidized bed in order to provide additional cross-linking of the wall materials. The dried air-containing microcapsular product is collected, mixed with inorganic pigments, and the mixture is dispersed in an aqueous paint system.

The paint is applied to a substrate and the resulting paint film has excellent hiding power and resistance to water.

EXAMPLE 3

An aqueous solution of a 7 percent by weight styrene-maleic acid ammonium salt is prepared having a pH of 7.0 at 25° C. Meanwhile, a 20 percent by weight solution of a melamine-formaldehyde (50 percent by weight in xylene-butanol) in mineral spirits is prepared by simple dilution of the melamine-formaldehyde with the mineral spirits.

An oil-in-water emulsion is prepared in a highshear mixer, by admixing 100 grams of the melamine-formaldehyde in mineral spirits solution with 150 grams of the aqueous styrene-maleic acid copolymer solution at a temperature of 25° C.

Next, 10 milliliters of a 5 percent by weight solution of sulfamic acid is added to the emulsion and dispersed well therein. The emulsion is then heated at a temperature of 40° C. for a period of two hours to chemically react the styrene-maleic acid with the melamine-formaldehyde and form precursor microcapsules containing oil.

EXAMPLE 4

Clay and a latex binder is added to the microcapsular dispersion of Example 3 to form an aqueous paint formulation. Next, the resulting paint system is coated onto a substrate and the paint film is dried at a temperature of about 100° C. in order to drive the oily core material from the precursor capsules present in the paint film. The resulting paint film has excellent water resistance.

EXAMPLE 5

The procedure of Example 4 is repeated with the exception that the paint film is permitted to dry at ambient temperature.

As in the case of the prior example, the film has good resistance to water.

This invention has been described in detail with particular reference to the preferred embodiments thereof but it will be understood that variations and modifications can be effected within the spirit and scope of the invention as described hereinabove and as defined in the appended claims.

What is claimed is:

1. A paint formulation comprising pigment and a liquid vehicle, wherein the improvement comprises providing said paint formulation with organic pigment in the form of microcapsular opacifying agents, said microcapsular opacifying agents being produced by a process which comprises admixing
    (a) an oily solution comprising an oil-soluble, partially-condensed thermosetting condensation product in a water-immiscible oily material; and
    (b) an aqueous solution of a water-soluble polymeric material;
thereby forming an emulsion, said thermosetting condensation product and said water-soluble polymeric material being capable of interacting to form a solid, resinous material, subjecting said emulsion to conditions whereby said polymeric materials react to form precursor microcapsules having solid capsular walls about a nucleus of said oily material, and activating said microcapsules to provide microcapsular opacifying agents by expelling said oily core material and replacing said oily core material with air.

2. The paint formulation of claim 1 wherein said activation is conducted by heating said microcapsules at a temperature in the range of between about ambient temperature and about 180° C.

3. The paint formulation of claim 1 wherein said microcapsules are activated by being spray-dried.

4. A paint formulation of claim 1 wherein said precursor microcapsules have an average particle diameter below about 1 micron.

5. The paint formulation of claim 4 wherein said precursor microcapsules have an average particle diameter between about 0.25 and about 0.8 micron.

6. The paint formulation of claim 1 wherein said oil-soluble, partially condensed thermosetting condensation product is a formaldehyde condensation product.

7. The paint formulation of claim 6 wherein said formaldehyde condensation product is an oil-soluble melamine-formaldehyde or urea-formaldehyde.

8. The paint formulation of claim 7 wherein said oil-soluble melamine-formaldehyde is a butylated melamine-formaldehyde.

9. The paint formulation of claim 8 wherein said water-soluble polymeric material is a salt of a styrene-maleic acid copolymer, methylcellulose or polyvinyl alcohol.

10. The paint formulation of claim 9 wherein said water-soluble polymeric material is a styrene-maleic acid ammonium salt.

11. The paint formulation of claim 1, wherein said oily solution additionally contains a wax modifying agent.

* * * * *